US00PP30098P2

(12) United States Plant Patent
Jan Kraan

(10) Patent No.: US PP30,098 P2
(45) Date of Patent: Jan. 15, 2019

(54) ***HYDRANGEA* PLANT NAMED 'BOKRALIMS'**

(50) Latin Name: *Hydrangea paniculata*
Varietal Denomination: Bokralims

(71) Applicant: Kees Jan Kraan, Alphen aan den Rijn (NL)

(72) Inventor: Kees Jan Kraan, Alphen aan den Rijn (NL)

(73) Assignee: BOOT & CO BOOMKWEKERIJEN B.V., Boskoop (NL)

( * ) Notice: Subject to any disclaimer, the term of this patent is extended or adjusted under 35 U.S.C. 154(b) by 0 days.

(21) Appl. No.: 15/732,197

(22) Filed: Oct. 2, 2017

(51) Int. Cl.
*A01H 5/00* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea paniculata* named, 'Bokralims', that is characterized by its very compact plant shape, its sterile flowers that are conspicuously star-shaped, its sterile flower sepals that are concave in aspect, and its sterile flowers that are lime green in color that fade to red-purple to red in color.

2 Drawing Sheets

Botanical classification: *Hydrangea paniculata.*
Varietal denomination: 'Bokralims'.

CROSS REFERENCE TO A RELATED APPLICATION

This application is related to a European plant breeders' rights application filed on Aug. 31, 2017, application No. 2017/20123. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Hydrangea paniculata* and will be referred to hereafter by its cultivar name, 'Bokralims'. 'Bokralims' represents a new deciduous shrub grown for landscape use.

The new invention arose from an ongoing controlled breeding program conducted by the Inventor in Boskoop, The Netherlands with the main objectives of developing new cultivars of *Hydrangea paniculata* with a dense and compact plant habits and inflorescence panicles that are dense with unique coloration.

'Bokralims' was derived from open pollination in August of 2011 of *Hydrangea paniculata* 'Phantom' (not patented). The male parent is therefore unknown. 'Bokralims' was selected in July of 2017 as a single unique plant from amongst the resulting seedlings.

Asexual propagation of the new cultivar was first accomplished by stem cuttings in August of 2017 by the Inventor in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'Bokralims' as a unique cultivar of *Hydrangea.*

1. 'Bokralims' exhibits a very compact plant habit.
2. 'Bokralims' exhibits sterile flowers that are conspicuously star-shaped.
3. 'Bokralims' exhibits sterile flower sepals that are concave in aspect.
4. 'Bokralims' exhibits sterile flowers that are lime green in color that fade to red-purple to red in color.

The female parent of 'Bokralims', 'Phantom', differs in having a much taller plant height, sterile flowers are considerably more white in color and sterile flower sepals that are wider. 'Bokralims' can be most closely compared to *Hydrangea paniculata* 'Limelight' (U.S. Plant Pat. No. 12,874) and *Hydrangea paniculata* 'Jane' (U.S. Plant Pat. No. 22,330). 'Limelight' and 'Jane' are both similar to 'Bokralims' in overall plant shape and overall inflorescence shape. 'Limelight' differs from 'Bokralims' in having a much taller plant height, sterile flower sepals are wider and considerably more white in color and fade to light purple in color. 'Jane' differs from 'Bokralims' in having a shorter plant height and sterile flowers sepals that are slightly whiter in color.

BRIEF DESCRIPTION OF THE DRAWINGS

The accompanying colored photographs illustrate the overall appearance and distinct characteristics of the new *Hydrangea*. The photographs were taken of a 3 year-old plant as field grown in Boskoop, The Netherlands.

The photograph in FIG. 1 provides a view of the plant habit of 'Bokralims' in bloom.

Figure 1:
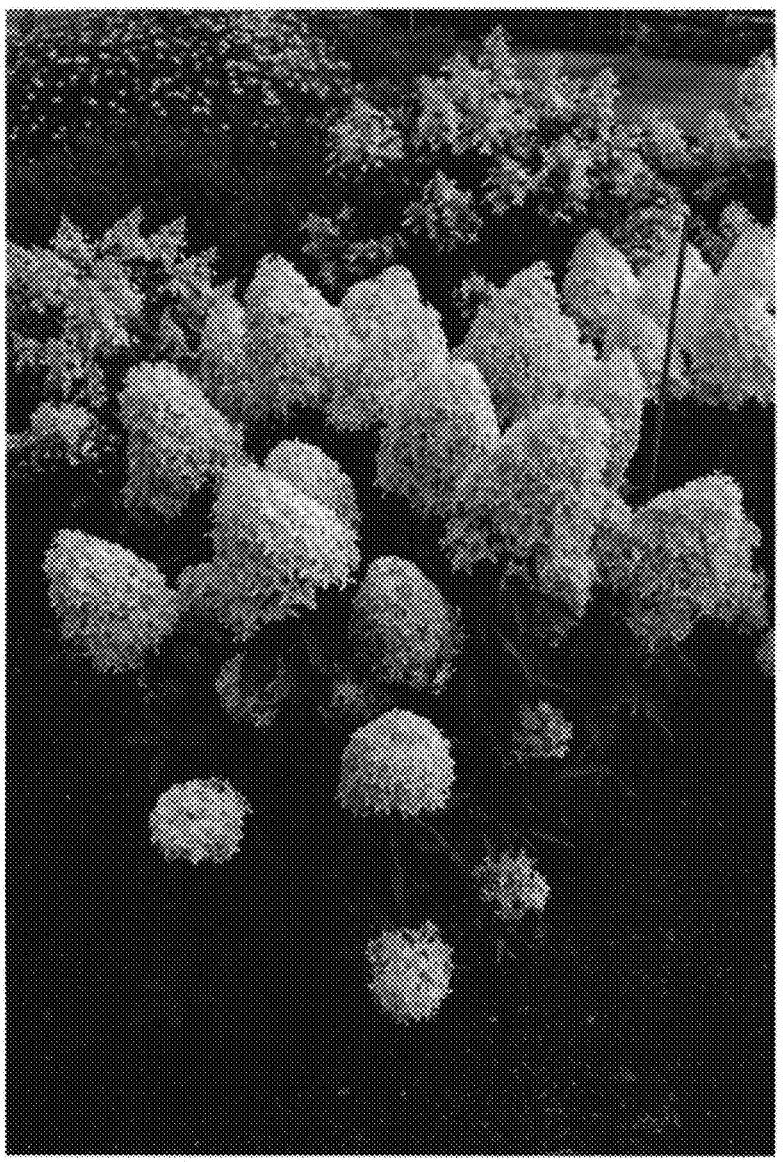
Figure 2:
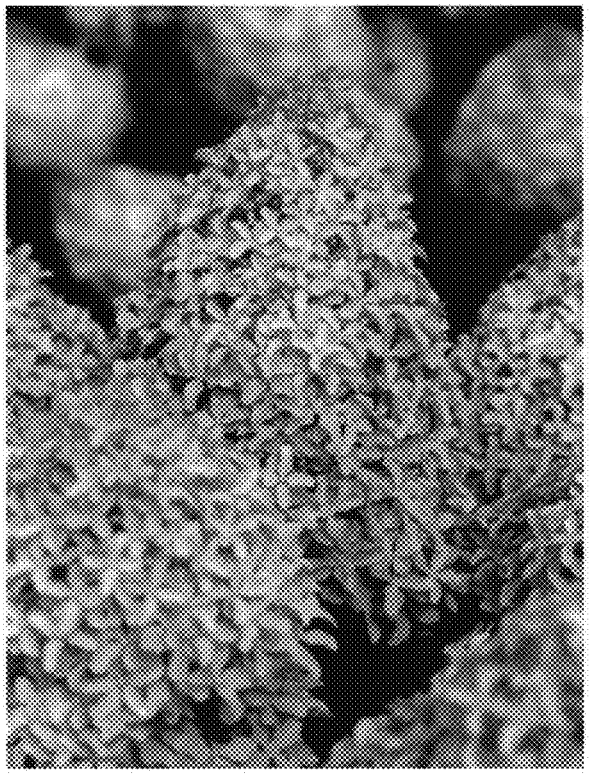

The photograph in FIG. 2 provides a close-up view of the inflorescences of 'Bokralims'.

Figure 3:
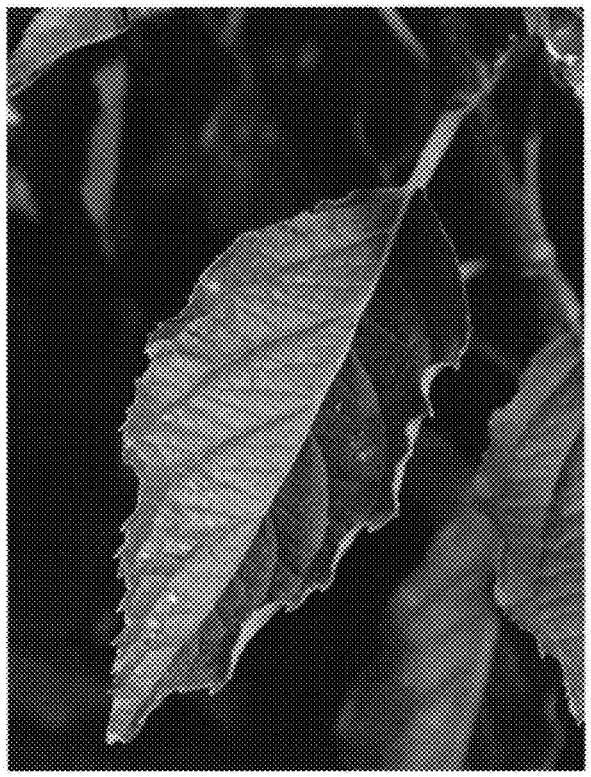

The photograph in FIG. 3 provides a close-up view of a leaf of 'Bokralims'.

The colors in the photographs are as close as possible with the photographic and printing technology utilized and the color values cited in the Detailed Botanical Description accurately describe the colors of the new *Hydrangea.*

DETAILED BOTANICAL DESCRIPTION

The following is a detailed description of the new cultivar as observed on 3 year-old plants as field grown outdoors in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—6 weeks from mid summer into early fall in The Netherlands.

*Plant type.*—Herbaceous shrub.

*Plant habit.*—Compact, dense, upright with strong erect stems.

*Height and spread.*—An average of 110 cm in height and 90 cm width as a 3 year-old plant in the landscape.

*Cold hardiness.*—At least in U.S.D.A. Zones 5 to 9.

*Diseases and pests.*—No susceptibility and resistance to diseases or pests has been observed.

*Root description.*—Fibrous.

*Propagation.*—Softwood stem cuttings.

*Root development.*—About 2 weeks to initiate roots, about 12 months to fully root as a young finished plant.

*Growth rate.*—Moderate.

Stem description:

*Shape.*—Round, solid.

*Stem color.*—New wood 146C, mature wood N199C, older bark 200D.

*Stem size.*—Average of 42.3 cm in length, 7.5 mm in diameter.

*Stem surface.*—Young stems moderately covered with short adpressed hairs and average of 0.1 cm in length, 156D in color, older stems rugose and bark-like.

*Stem aspect.*—Held at an average angle of 60° to soil level.

*Internode length.*—Average of 5.4 cm.

*Branching.*—An average of 36 branches.

*Lenticels.*—Moderately to densely covered with lenticels, an average of 0.2 cm in length, 157D in color on immature stems, N199D in color on mature stems.

Foliage description:

*Leaf shape.*—Ovate.

*Leaf division.*—Simple.

*Leaf base.*—Obtuse.

*Leaf apex.*—Apiculate.

*Leaf venation.*—Pinnate, upper surface color 147C, lower surface color N148D.

*Leaf size.*—An average of 9.8 cm in length, 5.4 cm in width.

*Leaf margins.*—Serrated.

*Leaf attachment.*—Petiolate.

*Leaf arrangement.*—Opposite and in whorls of three.

*Leaf surface.*—Upper and lower surfaces are smooth and rugose and moderately covered with short adpressed strigose hairs, 0.075 cm in length and 157D in color.

*Leaf color.*—Young upper surface 144A, young lower surface 146C, mature upper surface NN137A, mature lower surface 147B.

*Petioles.*—Average of 1.9 cm in length and 2.5 mm in width, color; upper surface 151A, margins 165B, lower surface 151A, both surfaces matte and moderately covered with short adpressed hairs, average of 0.05 cm in length and 157D in color.

Flower description:

*Inflorescence type.*—Broad pyramidal panicles, conical in shape, consists of sterile and fertile flowers.

*Lastingness of inflorescence.*—Sterile; persistent, fertile; self-cleaning.

*Inflorescence size.*—Average of 21.8 cm in length and 17.5 cm in width.

*Inflorescence number.*—One per stem.

*Flower number.*—An average of 600 sterile flowers and 840 fertile flowers per inflorescence.

*Fragrance.*—Moderately sweet and pleasant.

*Flower buds.*—Sterile flowers: obovate in shape, average of 5 mm in length and 6 mm in width, 150D in color, fertile flowers; obovate in shape, up to 3 mm in length and 2 mm in width, 157D in color, top 63A in color, glabrous surface for both.

*Peduncles.*—Average of 23.9 cm in length and 6 mm in width, 145B in color, pubescent surface, strong.

*Pedicels.*—Sterile flowers; 1.4 cm in length, 1 mm in diameter, held at an average angle of 50°, moderately strong, surface is matte and moderately covered with thin pubescence an average of 0.3 mm in length and too small to measure color, 145C in color, fertile flowers; and average of 2 mm in length and 1 mm in width, moderately strong, 155C in color, surface is matte, moderately to densely covered with thin pubescence, average of 0.2 mm in length and too small to measure color.

*Flowers.*—Sterile; rotate, lasting about 6 weeks on the plant, upright to outward and slightly drooping, more drooping when fading, 2.6 cm in diameter, 6 mm in depth,

*Petals.*—Sterile; 4 to occasionally 5, rotate, ovate to moderately concave in shape, acute tip, cuneate base, entire margins, 2 mm in length, 1.5 mm in width, both surfaces slightly glossy to matte, color when opening and fully open upper and lower surface NN155D, fertile; rotate, petals strongly reflexed and dropped when. maturing, lasting about 5 days, upright to outward, 7 mm in diameter, 6 mm in depth, fertile; 4 to occasionally 5, rotate, ovate to concave in shape, acute apex, cuneate base, entire margins, 3 mm in length, 1.5 mm in width, upper surface glabrous and slightly glossy, lower surface glabrous and matte, when opening upper and lower surface 155C, when fully open; dropped when maturing.

*Sepals.*—Sterile; 4 to occasionally 5, rotate, ovate to obovate, concave in aspect, obtuse tip, cuneate base, entire margins, 1.5 cm in length, 8 mm in width, both surfaces glabrous and matte, color; when opening upper surface between 150C and 151D, when opening lower surface 150D, when fully open upper surface 150C, when fully open lower surface 145D, tinged towards the margins 63D, upper surface fading to 145A to 145C and tinged with 60D, lower surface fading to 60D and tinged with 146D, fertile; 5, rotate, near triangulate in shape, acuminate apex, broad cuneate base, entire margins, 1 mm in length and width, both surfaces glabrous and matte, color; when opening and fully open upper and lower surface 157D.

Reproductive organs:

*Stamens*.—Sterile flowers; average of 8, anther; oblong in shape, 0.5 mm in length and 155A in color, filament; average of 2 mm in length and NN155D in color, pollen is moderate in quantity and 160D in color, fertile flowers; average of 10, anther; oblong in shape, 0.5 mm in length, 155A in color, filament; 4.5 mm in length, 155C in color, moderate amount of pollen, 160D in color.

*Pistils*.—Sterile flowers; no gynoecium present, fertile flowers; average of 3, occasionally 2, average of 1 mm in length, stigma; club-shaped, NN155D in color, style; 0.5 mm in length, 155C in color, ovary; 157A in color.

*Fruit and seed*.—None observed to date.

It is claimed:

1. A new and distinct cultivar of *Hydrangea* plant named 'Bokralims' as herein illustrated and described.

* * * * *